United States Patent [19]

Hilal et al.

[11] Patent Number: 4,597,766
[45] Date of Patent: Jul. 1, 1986

[54] IMPLANTABLE BIOPROSTHETIC TENDONS AND LIGAMENTS

[75] Inventors: Said S. Hilal, Laguna Niguel; Aws Nashef, Costa Mesa, both of Calif.

[73] Assignee: American Hospital Supply Corporation, Evanston, Ill.

[21] Appl. No.: 665,546

[22] Filed: Oct. 26, 1984

[51] Int. Cl.⁴ .............................................. A61F 1/24
[52] U.S. Cl. ..................................... 623/13; 623/16; 128/92 C; 128/92 G
[58] Field of Search ................................. 3/1, 1.9, 1.4; 128/92 C, 92 G; 623/1, 16, 13

[56] References Cited

U.S. PATENT DOCUMENTS 3,973,277  8/1976  Semple et al. .............................. 3/1
4,402,697  9/1983  Pollock et al. ........................... 3/1.4
4,467,478  8/1984  Jurgutis ...................................... 3/1

OTHER PUBLICATIONS

Goran, et al., "Fracture Dislocation of the Cervical Spine", Spine, vol. 3, Jun. 1978, pp. 95-102.

Primary Examiner—Richard J. Apley
Assistant Examiner—David J. Isabella
Attorney, Agent, or Firm—Perman & Green

[57] ABSTRACT

A tendon or ligament bioprosthesis comprised of a naturally occurring tendon or ligament isolated from an animal source, tanned with a bifunctional reagent capable of cross-linking biological tissue, at least one end of the tendon or ligament having attached thereto an intact decalcified chip of the bone from which the tendon or ligament was isolated. The presence of the decalcified bone chip provides a substrate which is receptive to the ingrowth of bone tissue when the bioprosthesis is implanted in a resected bone.

6 Claims, 3 Drawing Figures

IMPLANTABLE BIOPROSTHETIC TENDONS AND LIGAMENTS

BACKGROUND OF THE INVENTION

1. Field of the Invention

This present invention relates to a method for permanently anchoring implantable bioprosthetic tendons and ligaments to the bone of a host animal.

2. The Prior Art

The treatment of injured ligaments and tendons remains a serious clinical problem. Inadequately repaired damage to these structures results in pain, loss of function, and, in some cases, degenerative arthritis, and, when severely damaged by trauma or disease, fibrous tissue repair is often impossible. Many researchers have suggested the use of replacement structures for such damaged tissue. At this time, however, a completely successful prothesis for use in a chronic implantation has not been successful. Artificial prosthesis, as for example fabricated from a flexible elastomeric material such as silicone rubber or dacron fabric, although strong and durable, suffers from a lack of biocompatibility with the bone tissue onto which the artificial implant is anchored. Although bioprosthetic tendons and ligaments derived from animal sources possess such desirable properties as biocompatibility, strength and lack of adhesion to adjacent structures, this latter property makes it difficult to provide means of attaching the bioprosthesis to bone, tendon or muscle, which permanent attachment is dependent upon tissue ingrowth.

For example, intraarticular reconstruction of anterior and posterior cruciate ligaments of the knee generally involve drilling holes through the tibia and femur, followed by threading of a bioprosthetic ligament through the central channel, and stapling of the bioprosthetic ligament to the outer surface of the bone adjacent the resected channel. After implantation, the bone grows around the implanted ligament during the healing process to anchor the implanted ligament to the bone. However, experience with such a reconstruction technique has indicated that the bone growth is only marginally adherent to the ligament and, once the staples are removed, permanent anchoring of the ligament onto the bone is seldom achieved.

SUMMARY OF THE INVENTION

This invention relates to improvements in bioprosthetic ligaments and tendons having as its object, a bioprosthesis which provides permanent, strong anchoring of the bioprosthesis on the bone onto which it is implanted. A further object of the invention is a tendon or ligament bioprosthesis which is of increased strength and durability.

These objects are accomplished by the method of the present invention wherein an implantable naturally occurring ligament or tendon section is isolated from an animal source intact with a stump or chip of the bone to which it was originally attached. The isolated ligament or tendon section with attached bone chip is subjected to glutaraldehyde tanning in order to produce crosslinking of the collagen fibrils therein so as to increase the strength of the isolated ligament or tendon section. The bond chip is subjected to a decalcification treatment to place the chip in a more pliable state. The tanned ligament or tendon with intact decalcified bone chip is threaded through a channel of resected bone, the walls thereof having internal dimensions sufficient to allow threading of the tendon or ligament therethrough and to receive and retain the bone chip attached to the ligament or tendon.

The presence of the decalcified bone chip attached to the tendon or ligament encased within the walls of the bone channel when the tendon or ligament bioprosthesis is implanted in the resected bone provides, during the healing process, a substrate which is more receptive to the ingrowth of bone tissue when compared to the tendon or ligament substrate. This more favorable receptivity of the bone chip to tissue ingrowth creates a bond of strong attachment between the bone channel and the bone chip attached to the tendon or ligament which will withstand the stresses imposed on the implantation without causing injury to the implanted bioprosthesis.

DETAILED DESCRIPTION OF THE INVENTION

Figure 1:
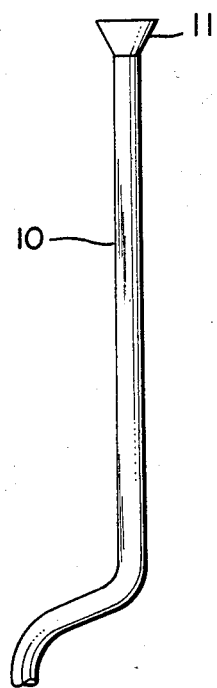
FIG. 1 is an isolated view of a ligament implantable bioprosthesis having an attached bone chip.

In accordance with the present invention, there is shown in FIG. 1 a surgically implantable tendon or ligament bioprosthesis having attached thereto a stump or chip of the bone to which the natural ligament or tendon was originally attached.

By way of example, the implantable bioprosthetic ligament may be inserted into the tibia and femur of a mammal for anterior and posterior cruciate ligament intraarticular reconstruction of the knee. The presence of the attached bone portion in the ligament implant promotes improved adhesion to the resected bone surface, whereby the implanted ligament exhibits improved anchoring on the resected bone surface.

Figure 2:
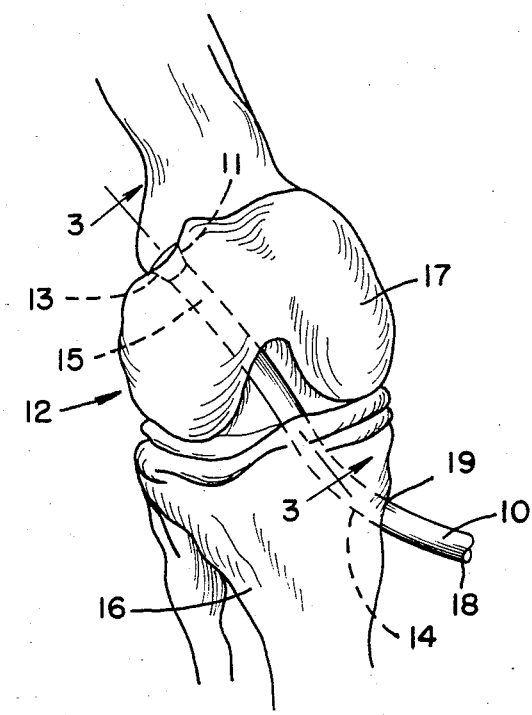
FIG. 2 is a front elevational view of a human knee having a cruciate ligament bioprosthesis with attached bone chip implanted therein in accordance with the present invention.
Figure 3:
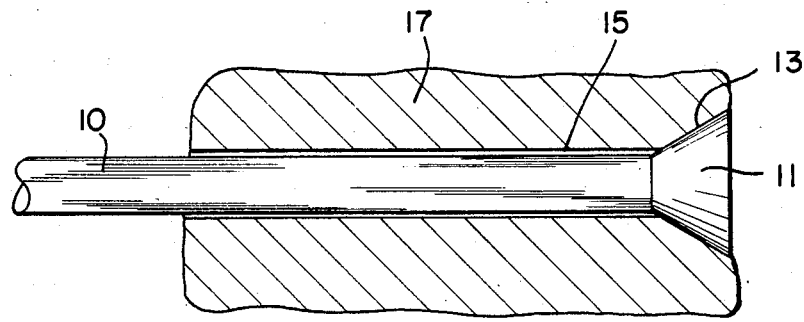
FIG. 3 is a sectional view of the ligament bioprosthesis within the resected channel of the femur, taken along line 3—3 of FIG. 1.

For the purpose of illustrating the present invention, there is shown in FIG. 1, a cruciate bioprosthetic ligament 10 having an attached bone chip 11 which has been shaped, upon removal from the bone of a sacrificed animal, into a tapered cylindrical plug. As shown in FIGS. 2 and 3 of the drawings, the implantable bioprosthetic ligament 10 having an intact bone chip 11 attached thereto is implanted in the knee 12 by drilling channels 14 and 15 through the tibia 16 and femur 17 respectively. A recess 13 adapted to receive and retain the bone chip is formed in the entrance edge of the bone channel 15 to promote nesting of the bone chip 11 in the walls of the channel 15.

The implant 10 is shown having its truncated end 18 extending outwardly from the resected bone channel edge 19; however, it is to be understood that this end is conventionally secured to the tibia 16 by stapling and the like during reconstructive surgery, which does not constitute part of the present invention and will not be further described.

In the broadest aspects of the present invention, the term implantable bioprosthesis describes any biological tissue which can be isolated from animal sources with a piece of its natural attachment to the original bone and which can be used to replace comparable materials in the human body. These include, but are not limited to, naturally occurring tendons, ligaments cruciate ligaments and lateral ligaments. The tissue can be derived from various animal sources such as, but not limited to bovine, porcine, equine, ovine or marsupial.

The method of the present invention also includes the step of tanning of the implantable bioprosthesis prior to implantation in the resected bone. Thus, in accordance with the present invention, the naturally occurring biological tissue such as a ligament or tendon is removed from its host along with a portion of the bone of the host animal attached thereto, and the attached bone chip is shaped to the proper dimensions required for implantation. The biological tissue is then fixed (tanned) with a biofunctional reagent capable of cross-linking biological tissue such as about 0.2 to about 0.8 weight percent and preferably from about 0.5 to about 0.7 percent glutaraldehyde in either phosphate-buffered solutions or phosphate-free buffers. Other bifunctional cros-linking agents may be substituted for glutraldehyde to fix the biological tissue, such cross-linking agents including acroylein and diimidio esters of varying carbon chain lengths. The tissue handling conditions as conventionally known are not considered part of the present invention unless otherwise stated.

In accordance with the present invention, it is preferable to tan the tissue within a tissue-stabliziing pH range; that is, within a pH range that is not deleterious to the tissue components. A preferred pH range is from about 7.0 to about 7.6, and a more preferred pH range is from about 7.1 to about 7.4. The most preferred pH in accordance with the present invention is 7.3.

Buffers which may be used in accordance with the present invention are preferably stable, non-interacting with the stabilization process, and have a buffering capacity sufficient to maintain an acceptable pH, particularly during the tanning of the tissue. The choice of the appropriate buffer, and its concentration will depend upon specific tissue preparation conditions, variations of which have been introduced by several manufacturers. The buffers can be either conventional 0.01–0.02M phosphate-buffered saline (PBS) or phosphate-deficient solutions such as those containing less phosphate than these 0.01 to 0.02M PBS solutions, and preferably less than about 0.001 to about 0.002M phosphate. Preferred buffers in accordance with the present invention include borate, carbonate, bicarbonate, cacodylate (found to be non-toxic in animals), and other synthetic, artificial, or organic buffers such as HEPES, N-2-hydroxyethylpiperazine-N'-2-ethanesulphonic acid; MOPS, 2-(N-morpholino) propane-sulfonic acid; and PIPES, 1,4-piperazinediethanesulphonic acid.

Preferably, the buffered or unbuffered solutions, used in accordance with the present invention, should not interfere with the tissue stabilizing process afforded by the glutaraldehyde tanning agent; that is, they should not react with the tanning agent or prevent the tanning agent from achieving proper fixation of the tissue. Illustrative of this are buffers containing primary and secondary amines such as tris(hydroxymethyl)aminomethane (Tris), which are known to react with the aldehyde groups of glutaraldehyde and thus interfere with the normal tissue stabilization process.

The method of the present invention further includes decalcification treatment of the bone chip attached to the implantable bioprosthesis prior to implanation. Decalcification places the bone tissue in a more flexible state, allowing the bone tissue to conform better to the uneven surface of the resected bone. Decalcification treatment of the attached bone tissue involves immersing the tissue in a 0.1% acidified solution of ethylene diamine tetraacetic acid (EDTA) at a pH of approximately 0.8 to 1.2 for a time period of 12–24 hours. Larger bone pieces may require longer immersion periods.

In accordance with the present invention, successful implantation of a bioprosthesis of the present invention on resected bone adjacent to a knee was achieved using glutaraldehyde tanned ligaments having an intact decalcified bone chip attached thereto. The bioprosthesis was threaded through holes drilled in the tibia and femur. Thus a hole having a diameter of 3/16 inch was drilled in the tibia and femur of a rabbit adjacent the knee. The bone chip was trimmed to the actual size of the hole, allowing the chip to seat in the hole. The chip was then anchored in place with sutures.

After a healing period of approximately 12 weeks, the implanted bioprosthesis was examined. The examination of the implant indicated that bone chip was well incorporated within the host bone with excellent apposition to the bone surface with no sign of rejection or necrosis.

While specific components of the present system are defined above, many other variables may be introduced which may in any way affect, enhance or otherwise improve the system of the present invention. These are intended to be included herein.

Although variations are shown in the present application, many modifications and ramifications will occur to those skilled in the art upon a reading of the present disclosure. These, too, are intended to be included herein.

We claim:

1. A tendon or ligament bioprosthesis comprised of a naturally occurring tendon or ligament isolated from an animal source, tanned with a bifunctional reagent capable of cross-linking biological tissue, at least one end of the tendon or ligament having attached thereto an intact pliable decalcified chip of the bone from which the tendon or ligament was isolated wherein said bioprosthesis is threaded through a channel of resected bone and said chip being shaped to be received and retained in a recessed opening of said bone thereby affixing said bioprosthesis within said channel.

2. The bioprosthesis of claim 1 wherein the tendon or ligament is tanned with gluteraldehyde.

3. The bioprosthesis of claim 2 wherein the tendon or ligament is tanned with a solution containing about 0.2 to about 0.8 weight percent of said glutaraldehyde.

4. A method of implanting a tendon or ligament bioprosthesis in a bone to effect an anchoring of the bioprosthesis on the bone which comprises isolating from an animal bone a tendon or ligament intact with a chip of the bone from which it was isolated, tanning the ligament or tendon with a bifunctional reagent capable of cross-linking biological tissue, decalcifying the chip to place the chip in a pliable state and threading the tanned ligament or tendon with the intact, decalcified, pliable bone chip through a channel of resected bone having internal dimensions sufficient to allow threading of the ligament or tendon therethrough and to receive and retain the bone chip.

5. The method of claim 4 wherein the tendon or ligament is tanned with a bifunctional reagent comprised of solution containing about 0.2 to about 0.8.

6. The method of claim 4 wherein the bone chip is shaped to be nested in a recessed opening of the resected bone.

* * * * *

UNITED STATES PATENT AND TRADEMARK OFFICE
CERTIFICATE OF CORRECTION

PATENT NO. : 4,597,766

DATED : July 1, 1986

INVENTOR(S) : Hilal, S and Nashef, A.

It is certified that error appears in the above—identified patent and that said Letters Patent is hereby corrected as shown below:

In Claim 5, Column 4, line 64 of the Patent insert --weight percent glutaraldehyde-- before the period.

Signed and Sealed this

Thirtieth Day of September 1986

[SEAL]

Attest:

DONALD J. QUIGG

Attesting Officer

Commissioner of Patents and Trademarks